United States Patent
Yamazaki

(10) Patent No.: US 9,442,280 B2
(45) Date of Patent: Sep. 13, 2016

(54) OPERATION MICROSCOPE

(75) Inventor: Toshio Yamazaki, Tokyo (JP)

(73) Assignee: MITAKA KOHKI CO., LTD., Tokyo (JP)

( * ) Notice: Subject to any disclaimer, the term of this patent is extended or adjusted under 35 U.S.C. 154(b) by 296 days.

(21) Appl. No.: 13/881,182

(22) PCT Filed: Oct. 28, 2011

(86) PCT No.: PCT/JP2011/074904
§ 371 (c)(1),
(2), (4) Date: Apr. 24, 2013

(87) PCT Pub. No.: WO2012/057303
PCT Pub. Date: May 3, 2012

(65) Prior Publication Data
US 2013/0222897 A1    Aug. 29, 2013

(30) Foreign Application Priority Data
Oct. 29, 2010  (JP) ................... 2010-244080

(51) Int. Cl.
*G02B 21/22*   (2006.01)
*G02B 21/00*   (2006.01)
(Continued)

(52) U.S. Cl.
CPC ........... *G02B 21/22* (2013.01); *G02B 21/0012* (2013.01); *A61B 1/043* (2013.01); *A61B 5/0071* (2013.01)

(58) Field of Classification Search
USPC .................. 359/368–390, 831–837, 431
See application file for complete search history.

(56) References Cited

U.S. PATENT DOCUMENTS

| | | | | |
|---|---|---|---|---|
| 4,852,955 A | * | 8/1989 | Doyle .................... | G01N 21/35 250/339.08 |
| 5,052,789 A | * | 10/1991 | Kleinberg .............. | G02B 21/18 359/375 |
| 5,668,661 A | * | 9/1997 | Tomioka ................ | G02B 21/22 359/368 |

(Continued)

FOREIGN PATENT DOCUMENTS

| | | |
|---|---|---|
| JP | 2003-50356 | 2/2003 |
| JP | 2003-511174 | 3/2003 |

(Continued)

OTHER PUBLICATIONS

IPRP for PCT/JP2011/074904, English language translation, May 14, 2013.

(Continued)

*Primary Examiner* — Bumsuk Won
*Assistant Examiner* — Balram Parbadia
(74) *Attorney, Agent, or Firm* — Greenblum & Bernstein, P.L.C.

(57) ABSTRACT

An operation microscope includes: an ordinary light path that guides light from an observation target to an eyepiece; a first secondary light path branched off from the ordinary light path; a second secondary light path merging with the ordinary light path; an imaging unit that images the observation target using light from the first secondary path; a display unit that displays an image based on an image signal from the imaging unit toward the second secondary path; and a reflector provided at a branch point of the ordinary light path and the first secondary light path in such a manner as to be capable of pulling off the branch point, and that bends the ordinary light path by reflection. The first secondary light path extends from the branch point along an extension of the ordinary light path before being reflected.

2 Claims, 9 Drawing Sheets

(51) Int. Cl.
    *A61B 1/04*     (2006.01)
    *A61B 5/00*     (2006.01)

(56) References Cited

U.S. PATENT DOCUMENTS

| | | | | |
|---|---|---|---|---|
| 5,825,532 | A | * | 10/1998 | Mochizuki ............ G02B 21/365 348/75 |
| 5,825,533 | A | * | 10/1998 | Yonezawa .......... G02B 21/0044 359/372 |
| 5,865,829 | A | | 2/1999 | Kitajima ............................ 606/3 |
| 7,050,225 | B2 | * | 5/2006 | Nakamura ..................... 359/368 |
| 2002/0126375 | A1 | | 9/2002 | Spink et al. |
| 2003/0030899 | A1 | | 2/2003 | Nakamura |
| 2004/0105147 | A1 | | 6/2004 | Hermann et al. |
| 2004/0196548 | A1 | | 10/2004 | Mannss et al. |
| 2006/0012854 | A1 | * | 1/2006 | Sander .......................... 359/368 |
| 2007/0127115 | A1 | * | 6/2007 | Hauger et al. ................ 359/376 |
| 2008/0037113 | A1 | | 2/2008 | Nakamura |
| 2009/0190209 | A1 | * | 7/2009 | Nakamura .................... 359/375 |

FOREIGN PATENT DOCUMENTS

| | | |
|---|---|---|
| JP | 2004-163413 | 6/2004 |
| JP | 2004-272200 | 9/2004 |
| JP | 2004-529384 | 9/2004 |
| JP | 2008-6089 | 1/2008 |
| JP | 2008-036277 | 2/2008 |
| WO | 01/27659 | 4/2001 |
| WO | 02/084366 | 10/2002 |
| WO | 2008/001822 | 1/2008 |

OTHER PUBLICATIONS

International Search Report dated Jan. 31, 2012 with English language translation.

* cited by examiner

OPERATION MICROSCOPE

TECHNICAL FIELD

The present invention relates to an operation microscope which can switch between ordinary observation and fluorescence observation.

BACKGROUND ART

Photodynamic therapy applying a photosensitive substance to a lesion being difficult to identify, such as a tiny tumor tissue, has been drawing attention in the field of surgical operations using an operation microscope. This photosensitive substance has characteristics that the substance has affinity for a lesion such as a tumor, and is accumulated on the lesion when administered to a patient. The photodynamic therapy utilizes these characteristics and conducts a treatment by irradiating an affected part with excitation light and observing fluorescence emitted from the excited photosensitive substance.

PTL 1 discloses an operation microscope equipped with a light source for excitation light, which enables fluorescence observation using the excitation light in addition to ordinary observation using natural light.

CITATION LIST

Patent Literature

[PTL 1] JP 2004-163413 A

SUMMARY OF INVENTION

Technical Problem

When the fluorescence is feeble in the fluorescence observation, identification of a fluorescent location tends to be difficult because the light is attenuated by optical elements such as lenses and mirrors. When an imaging device such as a CCD camera is introduced, the identification of the fluorescent location becomes easier owing to higher sensitivity. Still, in an attempt to capture even feebler fluorescence, there remains a problem of a long exposure time required to obtain significant contrast. In such a case, a time lag between the identification of the fluorescent location and a treatment becomes problematic because the shape or position of a lesion is liable to change.

The present invention has been made in view of the aforementioned problems and an object thereof is to provide an operation microscope which enables fluorescence observation in a short time.

Solution to Problem

An aspect of the present invention is an operation microscope comprising: an ordinary light path configured to guide light from an observation target to an eyepiece; a first secondary light path branched off from the ordinary light path; a second secondary light path merging with the ordinary light path; an imaging unit configured to image the observation target using light from the first secondary path; a display unit configured to display an image based on an image signal from the imaging unit toward the second secondary path; and a reflector provided at a branch point of the ordinary light path and the first secondary light path in such a manner as to be capable of pulling off the branch point, and configured to bend the ordinary light path by reflection, wherein the first secondary light path extends from the branch point along an extension of the ordinary light path before being reflected.

It is preferable that the second secondary light path extends to the branch point along an extension of the ordinary light path after being reflected.

It is preferable that the second secondary light path is connected to the ordinary light path at a connection point located between the branch point and the eyepiece, and that the operation microscope further comprises a reflective plate configured to be inserted into the connection point when the reflector pulls out, and to reflect light from the second secondary light path to the ordinary light path.

Advantageous Effects of Invention

There is no light attenuation by the reflector in the fluorescence observation. Accordingly, it is possible to obtain a clear image and to perform observation in a short time.

BRIEF DESCRIPTION OF DRAWINGS

FIG. 10 is a view showing relations of a camera with display panels and the like.

DESCRIPTION OF EMBODIMENTS

[1st Embodiment]

Figure 1:
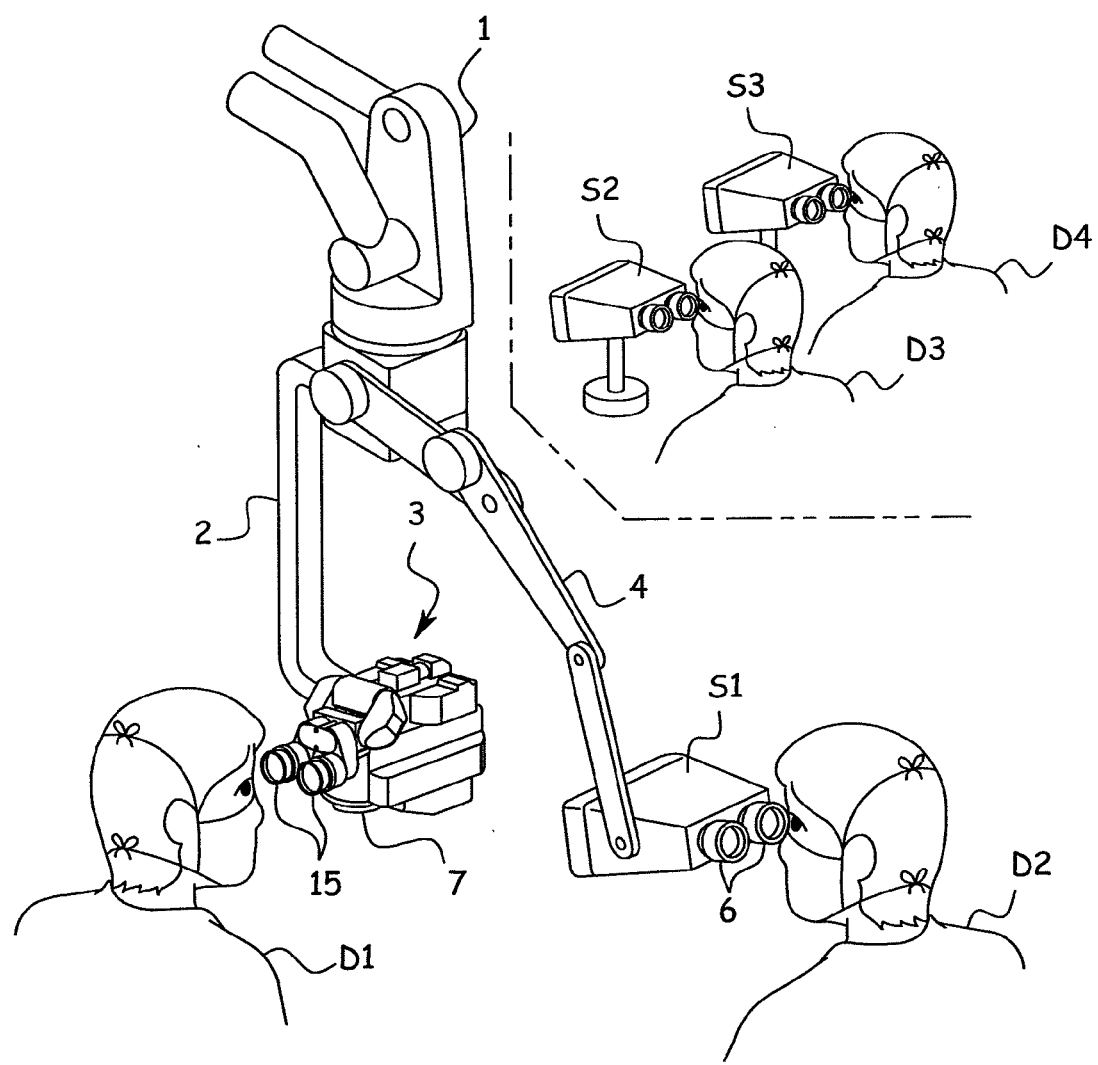
FIG. 1 is a perspective view showing a stereomicroscope and stereo viewers according to a 1st embodiment of the present invention.
Figure 2:
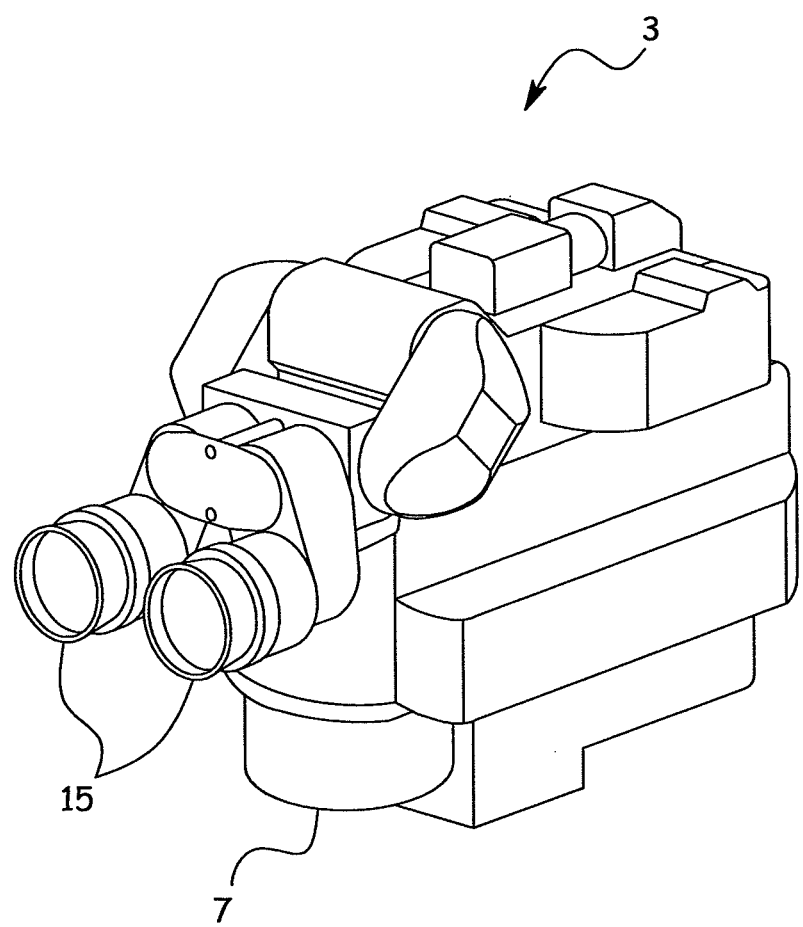
FIG. 2 is a perspective view showing the stereomicroscope.
Figure 3:
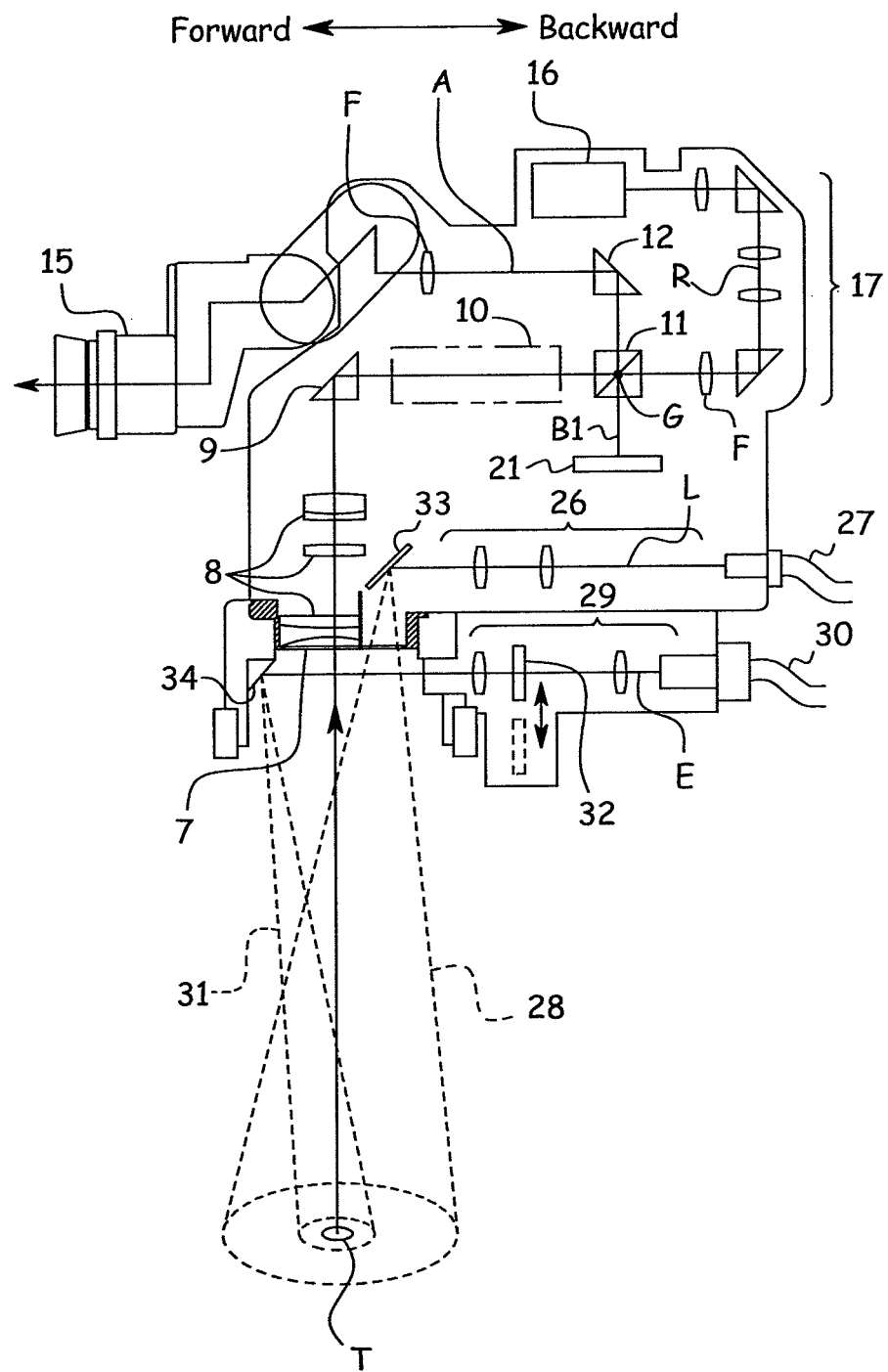
FIG. 3 is a view showing an internal structure of the stereomicroscope.
Figure 4:
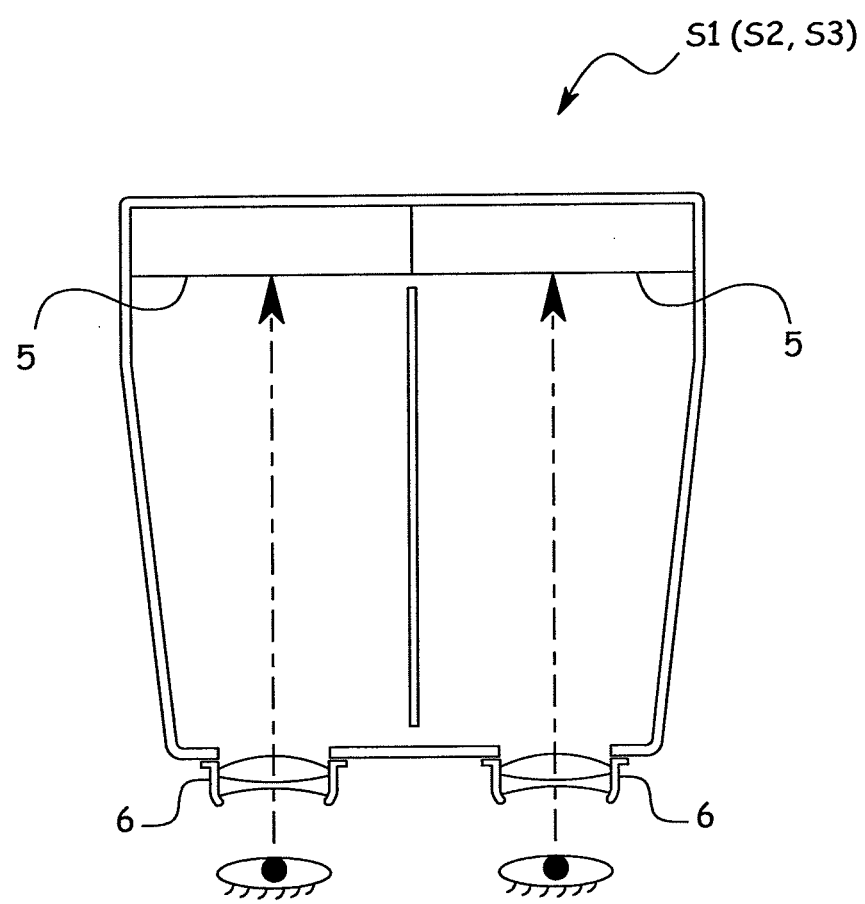
FIG. 4 is a view showing an internal structure of each stereo viewer.

FIG. 1 to FIG. 6 are views showing a stereomicroscope as an operation microscope according to this embodiment. As shown in FIG. 1, a substantially U-shaped support arm 2 is attached to a front-end link 1 of an unillustrated stand apparatus that is installed in an operating room, and a stereomicroscope 3 for a main operator D1 is supported at a lower end portion of the support arm 2.

Meanwhile, a stereo viewer S1 for an assistant D2, who takes a position on the right side of the main operator D1, is supported on the right side of the stereomicroscope 3. The stereo viewer S1 is supported by a retainer arm 4 extending from the front-end link 1. The stereo viewer S1 includes a pair of liquid crystal panels (which may be of a transmissive type or a reflective type) 5 located inside (see FIG. 4). Electronic images of an affected part T (see FIG. 3) acquired by the stereomicroscope 3 are displayed on the liquid crystal panels 5. The assistant D2 can watch the electronic images of the affected part T displayed on the liquid crystal panels 5 through eyepieces 6.

More stereo viewers S2 and S3 are installed in other places in the operating room whereby a nurse D3, a medical intern D4, and others can watch the electronic images of the affected part T.

Next, a structure of the stereomicroscope 3 will be described.

<Ordinary Light Path A>

Now, ordinary light paths A will be described first. In this embodiment, a pair of right and left pair ordinary light paths A are formed to enable stereoscopic observation. A light flux entrance 7 is formed in a lower part of the stereomicroscope 3. A group of lenses serving as an objective optical system 8 are formed in a vertical direction (an up-down direction on the sheet surface) above the light flux entrance 7 (see FIGS. 2 and 3). Prisms 9 are located above the objective optical system 8, and groups of lenses each serving as a horizontal zoom optical system 10 are arranged backward from the prisms 9.

Beam splitters 11 each serving as reflecting means or branching means are provided at branch points G behind the zoom optical systems 10. Each beam splitter 11 is formed, for example, by joining two triangular (right-angle) prisms each provided with a reflecting/transmitting film on one of reflecting surfaces, and has a cubic shape as a whole. Specifically, a reflecting/transmitting surface of the beam splitter 11 is formed into a plane including two ridge lines which defines a diagonal. In this embodiment, the reflecting/transmitting surface is inclined upward by 45° with respective to the ordinary light path A incident on the beam splitter 11. As a consequence, each beam splitter 11 bends the ordinary light path A, which proceeds horizontally, perpendicularly upward by reflection. At the same time, the beam splitter 11 transmits part of the ordinary light path A emitted from the zoom optical system 10 to an imaging light path R located behind.

The ordinary light paths A proceeding upward are bent horizontally forward via prisms 12, and are guided to eyepieces 15 through notch filters F. Each notch filter F has a characteristic to cut off excitation light 31 to be described later.

Figure 5:
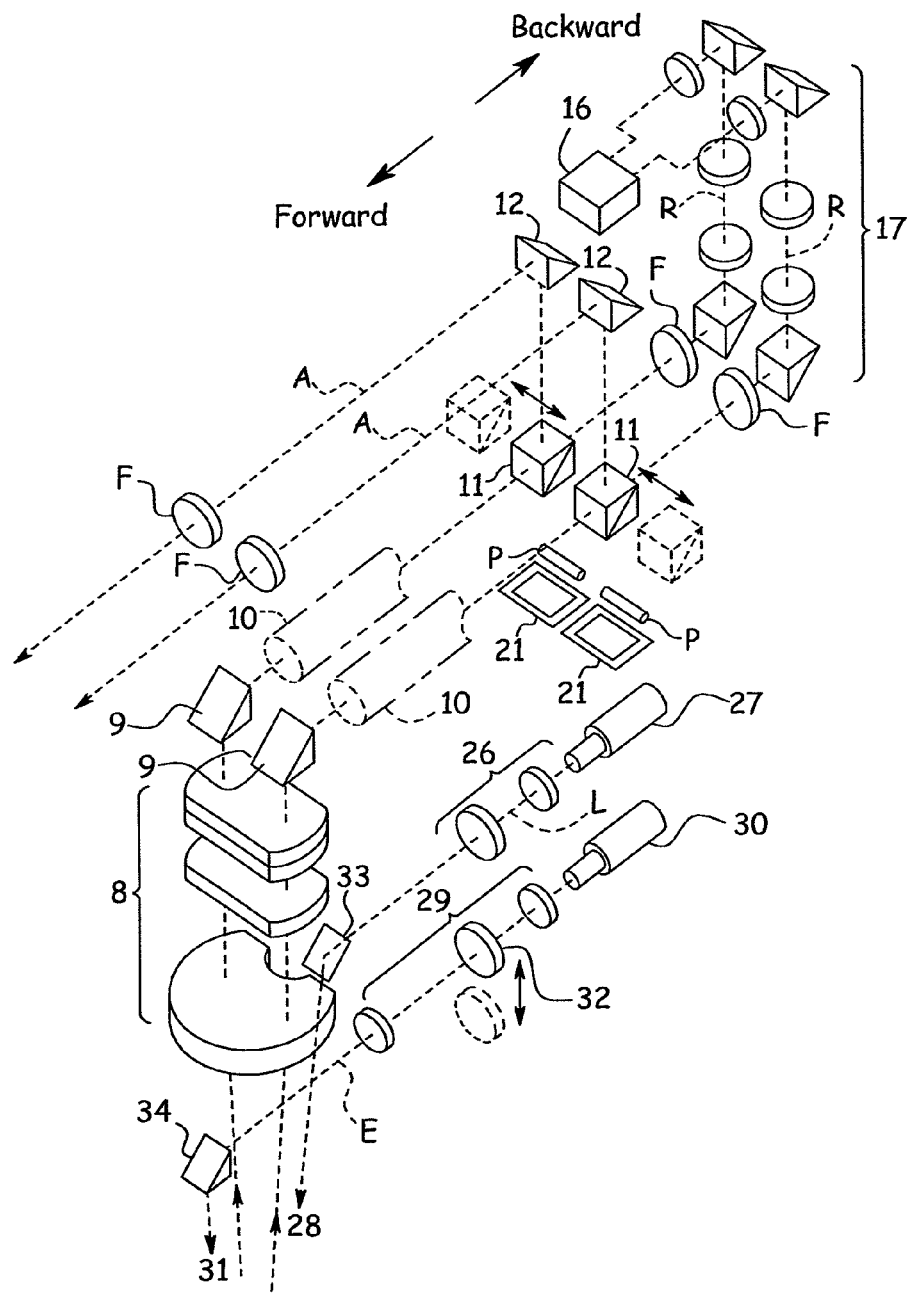
FIG. 5 is a view showing ordinary light paths of the stereomicroscope.
Figure 6:
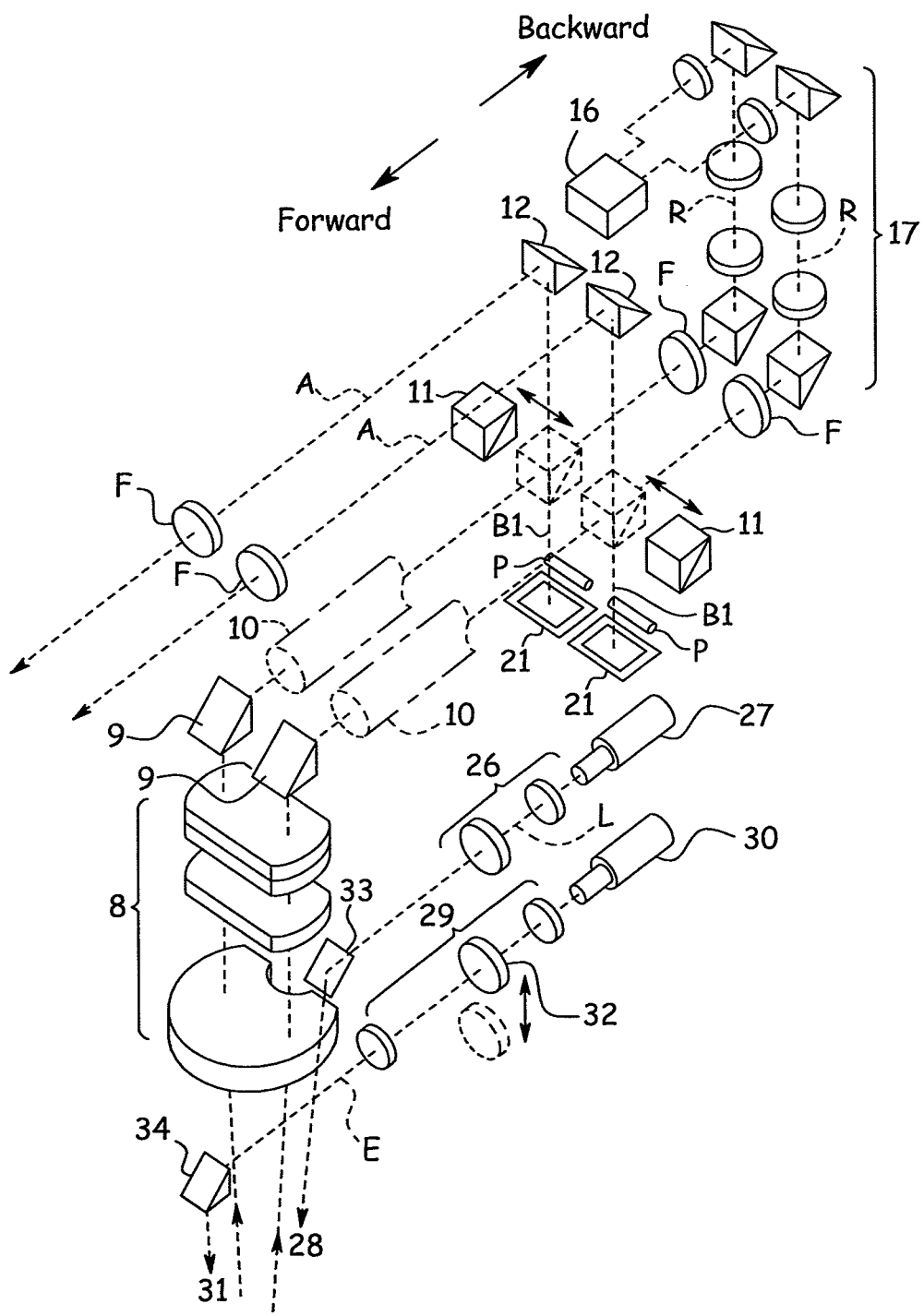
FIG. 6 is a view showing image light paths of the stereomicroscope according to the 1 embodiment of the present invention.

Each beam splitter 11 can pull completely out of the ordinary light path A and the imaging light path R with the assistance of a driving device (not shown). As shown in FIG. 5, for example, each beam splitter 11 moves to a corresponding position illustrated with dotted lines in a direction perpendicular to a plane that contains the ordinary light path A, the imaging light path R, and the branch point G, and thus pulls out of the ordinary light path A and the imaging light path R. When the beam splitter 11 pulls out of the branch point G, the ordinary light path A emitted horizontally from the zoom optical system 10 advances straight, thereby proceeding through the imaging light path R without suffering from light attenuation by the beam splitter 11.

<Imaging Light Path R>

Part of each ordinary light path A passes through the beam splitter 11 and is then guided to a camera 16 through the corresponding imaging light path R serving as a first secondary light path. The imaging light path R is situated on an extension of the ordinary light path A before being reflected by the beam splitter 11.

The imaging light paths R are provided with an imaging optical system 17. A notch filter F which is similar to the one provided on each ordinary light path A is provided between each beam splitter 11 and the imaging optical system 17.

When the beam splitters 11 pull out, the ordinary light paths A are similarly guided to the camera 16 via the imaging light paths R.

Here, the camera 16 includes a known stereo adapter (JP 2607828 B, for example), and this single camera can image an electronic image for the right eye and an electronic image for the left eye at the same time. As described above, when the single camera 16 or a single image pickup device (such as a CCD sensor) acquires the electronic images, it is easy to perform imaging because sensitivity adjustment between cameras is not required unlike in the case of using two cameras, for instance.

<Image Light Path B1>

Of extensions of each ordinary light path A reflected by the beam splitter 11, a display panel (a display unit) 21 is provided on an extension that extends in an opposite direction to the direction of the procession. This extension is an image light path B1 serving as a second secondary light path. Specifically, light from the display panel 21 goes through the image light path B1 and merges with the ordinary light path A at the branch point G. The display panels 21 are controlled by a controller 22, and display the pair of right and left electronic images that are imaged by the camera 16 (see FIG. 10). Each display panel 21 is a one-inch reflective LCD, for example, whose screen is illuminated by a light source P made of a white LED. The light source P is turned on when the beam splitter 11 pulls out of the branch point G and the image light path B1 performs its function.

When the beam splitter 11 pulls out of the branch point G, the image light path B1 is bent horizontally forward via the prism 12 as in the case of the ordinary light path A, and is guided to the eyepiece 15 via the notch filter F.

Figure 10:
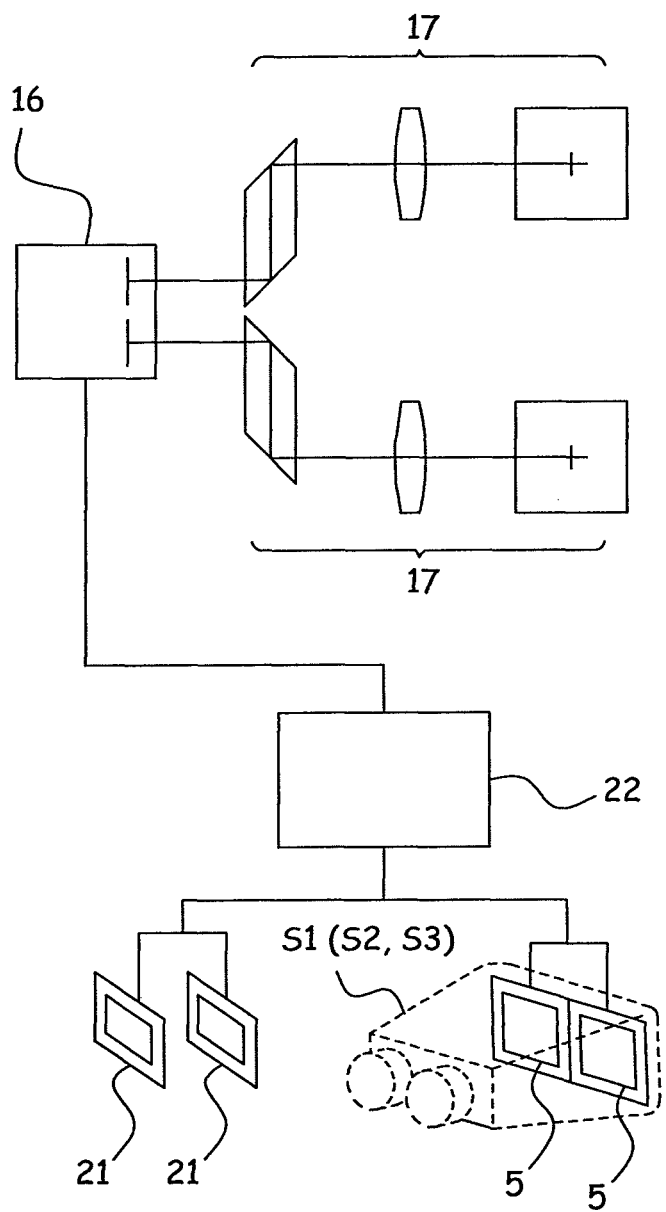

Here, the electronic images imaged by the camera 16 are also displayed on the liquid crystal panels 5 of the stereo viewers S1 to S3 via the controller 22 (see FIG. 10).

<Illumination Light Path L and Excitation Light Path E>

An illumination light path L and an excitation light path E are formed below the zoom optical systems 10. Illumination light 28 from a xenon lamp or the like is radiated from an optical fiber 27 to the illumination light path L via an illumination optical system 29. The illumination light 28 widely illuminates the periphery of the affected part T.

Excitation light 31 such as a laser or the like is radiated from an optical fiber 30 to the excitation light path E via an excitation optical system 29. The excitation light 31 narrowly illuminates the periphery of the affected part T. Only the excitation light 31 having a necessary wavelength is allowed to pass through a band pass filter 32. The band path filter 32 is freely insertable and retractable. The band pass filter 32 is retracted in the case of conducting a laser therapy, for example.

Next, operations will be described.

1. Ordinary Observation (see FIGS. 3 and 5)

In the case of ordinary observation, the beam splitters 11 are placed at the branch points G and light fluxes that passed through the objective optical system 8 are guided to the pair of right and left eyepieces 15 via the ordinary light paths A. Accordingly, the main operator D1 can stereoscopically observe optical images of the affected part T through the eyepieces 15. Meanwhile, since part of the light fluxes are branched off and imaged with the camera 16, the people other than the main operator D1 can see the electronic images with the stereo viewers S1 to S3. The optical images viewed through the eyepieces 15 maybe images under the illumination light 28 or fluorescence observation under the excitation light E. In the case of the fluorescence observation, a fluorescent substance such as talaporfin sodium or indocyanine green has to be accumulated on an affected part in advance. In the meantime, when the fluorescence is optically observed through the eyepieces 15, the operating room has to be darkened since the fluorescence is feeble. Here, when only the assistant D2 and others using the stereo viewers S1 to S3 observe the fluorescence, they can observe the feeble fluorescence by adjusting sensitivity of the camera 16 instead of darkening the operating room. When fluorescent images are seen by the naked eye or imaged with the camera 16, the excitation light 31 which is unnecessary for the fluorescence observation can be filtered out of the light paths by using the notch filters F. Thus, it is possible to observe and image vivid fluorescence.

2. Fluorescence Observation Using Display Panels 21 (see FIG. 6)

When the fluorescence at the affected part T irradiated with the excitation light 31 is imaged with the camera 16, and the resultant electronic images are displayed on the display panels 21 in the stereomicroscope 3 and watched through the eyepieces 15, the main operator D1 causes the beam splitters 11 to pull out of the branch points G by operating an unillustrated foot switch or the like, thereby switching the light paths to the imaging light paths R and the image light paths B1.

Thus, the fluorescent images displayed on the display panels 21 can be stereoscopically observed through the eyepieces 15. Since there is no light attenuation as a result of the pullout of the beam splitters 11, the bright and vivid fluorescent images can be observed promptly and stereoscopically. In general, the transmittance of the beam splitters 11 is equal to 50%. Accordingly, the intensity of the fluorescence received by the camera 16 is doubled as a result of the pullout of the beam splitters 11. In addition, the fluorescence is imaged with the camera 16 typically having higher sensitivity than sensitivity of the naked eye, and can therefore be observed more clearly than in the case of ordinary observation. Meanwhile, the fluorescence observation in various tones is enabled by adjusting the sensitivity of the camera 16. Thus, it is possible to perform observation in the optimum tones depending on various fluorescent substances.

Note that the stereoscopic observation with the display panels 21 is not limited only to the fluorescence observation under the excitation light 31, but may also be the ordinary image observation under the illumination light 28. In this case as well, there is no light attenuation as a result of the pullout of the beam splitters 11. Accordingly, the bright and vivid electronic images can be observed stereoscopically. Moreover, since the tone of the images is adjustable, it is possible to observe the electronic images in a different tone from that of optical observation. For example, it is possible to perform observation by changing the tone in such a manner that a region to be excised in an operation can be more clearly distinguished from the rest of regions compared with actual observation by the naked eye. The above-described observation under the excitation light 31 and the illumination light 28 can similarly be performed by the people other than the main operator D1 by using the stereo viewers S1 to S3.

In addition, the main operator D1 can switch between the optical observation and the image observation while keeping the eyes in contact with the eyepieces 15. Thus, the main operator D1 does not have to stop a procedure in the operation.

[2nd Embodiment]

Figure 7:
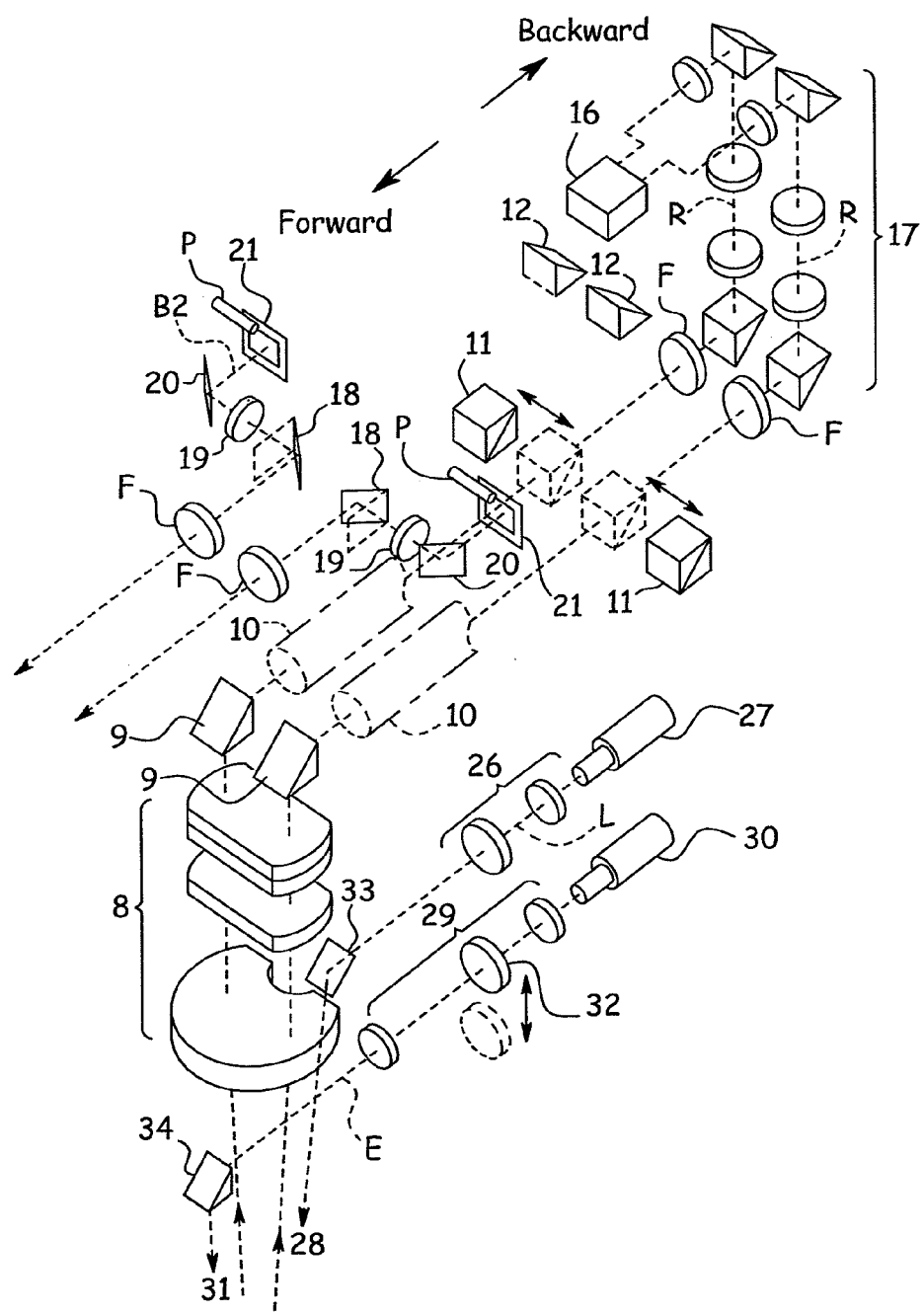
FIG. 7 is a view showing image light paths of a stereomicroscope according to a 2nd embodiment of the present invention.
Figure 8:
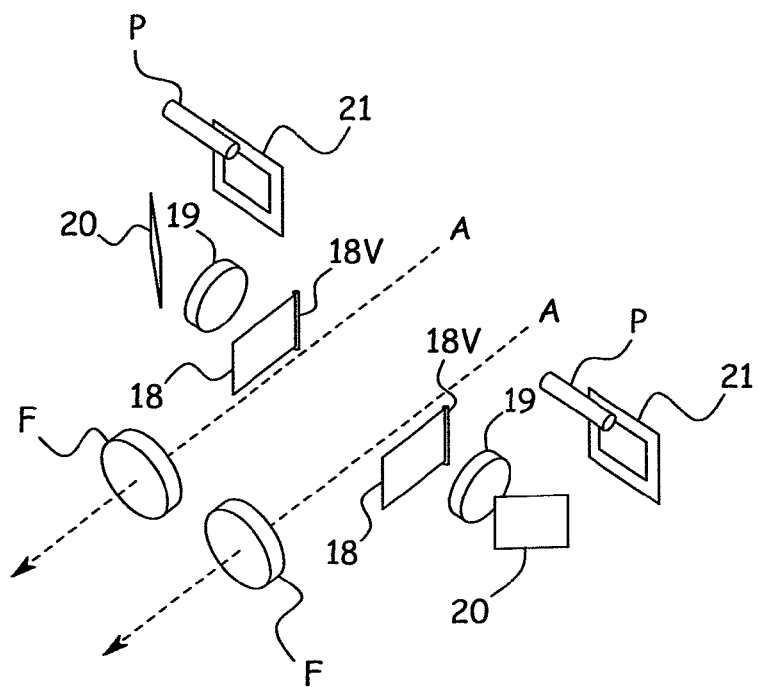
FIG. 8 is a perspective view showing turning mirrors at the image light paths.
Figure 9:
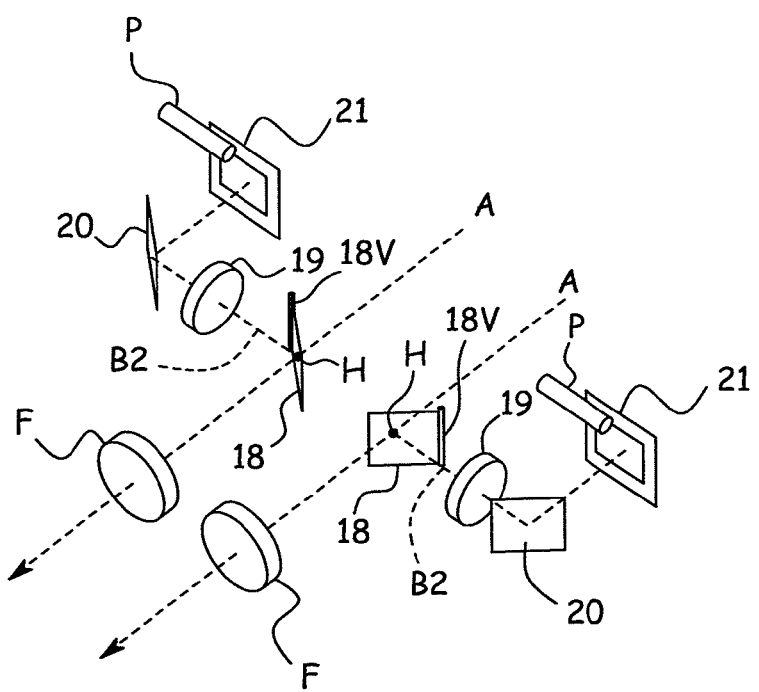
FIG. 9 is a perspective view corresponding to FIG. 8, which shows a state of turn of the turning mirrors.

FIG. 7 to FIG. 9 are views showing a 2nd embodiment of the present invention. This embodiment includes constituents similar to those of the 1st embodiment. Hence, those similar constituents will be denoted by common reference numerals and duplicate explanation will be omitted.

In this embodiment, image light paths B2 serving as second secondary paths B2 with the display panels 21 are formed instead of the image light paths B1 in the 1st embodiment.

<Image Light Path B2>

A turning mirror (a reflective plate) 18 is provided at a connection point H (see FIG. 9) located between the prism 12 and the notch filter F in each ordinary light path A. The turning mirror 18 can freely enter the ordinary light path A at an angle of 45° by being turned around an end vertical shaft 18V. An image light path B2 is branched off and hence formed from a portion corresponding to the turning mirror 18. The image light path B2 proceeds from the display panel 21 to the turning mirror 18 via a fixed mirror 20 and a lens 19, and merges with the ordinary light path A. Each turning mirror 18 simply has a structure to be turned around the end vertical shaft 18V while staying substantially in the same position. Accordingly, the turning mirrors 18 can be installed in a small space inside the stereomicroscope 3.

Operations of the ordinary observation in the 2nd embodiment are the same as the operations of the ordinary observation in the 1st embodiment. Specifically, the beam splitters 11 are placed at the branch points G, and the light fluxes passing through the objective optical system 8 are guided to the pair of right and left eyepieces 15 via the ordinary light paths A.

Meanwhile, in the case of performing the fluorescence observation with the image light paths B2 using the display panels 21, the main operator D1 moves an unillustrated foot switch or the like to cause the beam splitters 11 to pull out of the branch points G, and to locate reflecting surfaces of the turning mirrors 18 at the connection points H, thereby switching the ordinary light paths A from the branch points G to the connection points H into the imaging light paths R and the image light paths B2.

Thus, the fluorescent images displayed on the display panels 21 can be stereoscopically observed through the eyepieces 15. Since there is no light attenuation as a result of the pullout of the beam splitters 11, the bright and vivid fluorescent images can be observed promptly and stereoscopically. In general, the transmittance of the beam splitters 11 is equal to 50%. Accordingly, the intensity of the fluorescence received by the camera 16 is doubled as a result of the pullout of the beam splitters 11. In addition, the fluorescence is imaged with the camera 16 typically having the higher sensitivity than the sensitivity of the naked eye, and can therefore be observed more clearly than the case of the ordinary observation. Meanwhile, the fluorescence observation in various tones is enabled by adjusting the sensitivity of the camera 16. Thus, it is possible to perform observation in the optimum tones depending on various fluorescent substances.

Other effects similar to those in the 1st embodiment can also be achieved.

The invention claimed is:
1. An operation microscope comprising:
an ordinary light path configured to guide light from an observation target to an eyepiece;
a first secondary light path branched off from the ordinary light path;

a second secondary light path merging with the ordinary light path;

an imaging unit configured to image the observation target using light from the first secondary path;

a display unit configured to display an image based on an image signal from the imaging unit toward the second secondary path; and a reflector provided at a branch point of the ordinary light path and the first secondary light path in such a manner as to be capable of pulling off the branch point, and configured to bend the ordinary light path by reflection, wherein the first secondary light path extends from the branch point along an extension of the ordinary light path before being reflected, the second secondary light path is connected to the ordinary light path at a connection point located between the branch point and the eyepiece, and the operation microscope further comprises a reflective plate configured to be inserted into the connection point when the reflector pulls out, and to reflect light from the second secondary light path to the ordinary light path.

2. The operation microscope according to claim 1, wherein the second secondary light path extends to the branch point along an extension of the ordinary light path after being reflected.

* * * * *